(12) United States Patent
Plos et al.

(10) Patent No.: US 7,374,580 B2
(45) Date of Patent: May 20, 2008

(54) DYEING COMPOSITIONS COMPRISING A 1,2-INDANDIONE DERIVATIVE

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 332 days.

(21) Appl. No.: 11/151,278

(22) Filed: Jun. 14, 2005

(65) Prior Publication Data
US 2005/0283923 A1    Dec. 29, 2005

Related U.S. Application Data

(60) Provisional application No. 60/637,748, filed on Dec. 22, 2004.

(30) Foreign Application Priority Data
Jun. 14, 2004    (FR)    .................... 04 51267

(51) Int. Cl.
*A61K 7/13*    (2006.01)
(52) U.S. Cl. ................ 8/405; 8/406; 8/407; 8/408; 8/410; 8/421; 8/607; 568/303
(58) Field of Classification Search ........... 8/405, 8/406, 407, 408, 410, 421, 607; 568/303
See application file for complete search history.

(56) References Cited

U.S. PATENT DOCUMENTS

| 5,625,080 | A | | 4/1997 | Hughes |
| 6,127,189 | A | * | 10/2000 | Joullie et al. ............ 436/111 |
| 2005/0144740 | A1 | | 7/2005 | Gross et al. |

FOREIGN PATENT DOCUMENTS

| DE | 213455 | 10/1909 |
| DE | 43 17 855 | 12/1994 |
| DE | 43 35 625 | 4/1995 |
| DE | 197 17 222 | 10/1998 |
| DE | 197 45 355 | 4/1999 |
| DE | 198 45 481 | 4/2000 |
| DE | 102 41 076 | 3/2004 |
| EP | 1 010 419 | 6/2000 |
| EP | 1 013 259 | 6/2000 |
| EP | 1 300 134 | 4/2003 |
| WO | WO 95/11001 | 4/1995 |
| WO | WO 98/20344 | 5/1998 |
| WO | WO 99/18914 | 4/1999 |

OTHER PUBLICATIONS

STIC Search Report dated on Apr. 25, 2007.*
European Search Report for EP 05 29 1273, dated Oct. 24, 2005, Ex. S. Werner.
French Search Report for FR 04 51267, dated Jan. 24, 2005, Ex. S. Werner.
Joullie, et al. "Ninhydrin and Ninhydrin Analogs: Synthesis and Applications", Tetrahedron, vol. 47, No. 42, pp. 8791-8830, 1991.
Nalliah, et al. "The Total Synthesis of Ochrobirine", Canadian Journal of Chemistry, vol. 50, pp. 1819-1824, 1972.
Hark, "Synthesis of Ninhydrin Analogues", Dissertation in Chemistry, University of Pennsylvania, 1996.
Petrovskaia, "Design and Synthesis of Chromogenic and Fluorogenic Reagents for Amino Acid Detection", Dissertation in Chemistry, University of Pennsylvania, 1999.
Database Caplus 'Online! Chemical Abstracts Service, Columbus, Ohio, US; XP002314700, 1962.
English language Derwent Abstract of DE 43 17 855, Dec. 1, 1994.
English language Derwent Abstract of DE 43 35 625, Apr. 20, 1995.
English language Derwent Abstract of DE 197 17 222, Oct. 29, 1998.
English language Derwent Abstract of DE 197 45 355, Apr. 15, 1999.
English language Derwent Abstract of DE 198 45 481, Apr. 6, 2000.
English language Derwent Abstract of EP 1 010 419, Jun. 21, 2000.
English language Derwent Abstract of EP 1 013 259, Jun. 28, 2000.
English language Derwent Abstract of EP 1 300 134, Apr. 9, 2003.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The present disclosure relates to compositions for dyeing keratin materials, for example compositions for hair dyeing, comprising at least one 1,2-indandione derivative, a method for dyeing using such compositions, and a multicomponent dyeing agent used for carrying out such a method.

34 Claims, No Drawings

DYEING COMPOSITIONS COMPRISING A 1,2-INDANDIONE DERIVATIVE

This application claims benefit of U.S. Provisional Application No. 60/637,748, filed Dec. 22, 2004, the contents of which are incorporated herein by reference. This application also claims benefit of priority under 35 U.S.C. § 119 to French Patent Application No. 04 51267, filed Jun. 14, 2004, the contents of which are also incorporated by reference.

The present disclosure relates to compositions for dyeing keratin materials, for instance, compositions for hair dyeing comprising at least one 1,2-indandione derivative, a method for dyeing using such compositions, and a multi-component dyeing agent used for carrying out such a method.

For a long time, many people have sought to modify the color of their skin, of their eyelashes or of their hair, for example, to mask their grey hair. To do this, several technologies have been developed.

It is known to dye human keratin fibers, such as the hair, with dyeing compositions comprising oxidation dye precursors, generally called oxidation bases. These oxidation bases are colorless or slightly colored compounds which, when combined with oxidizing products, give rise, through a process of oxidative condensation, to colored compounds. These dyes are insoluble and are trapped inside the hair fiber.

It is also known that it is possible to vary the shades obtained with these oxidation bases by combining them with couplers or color modifiers. The variety of oxidation bases and couplers that can be used allows for a rich palette of colors to be obtained.

The colors obtained can exhibit good fastness to shampoo. However, the oxidation reaction occurs with the aid of oxidizing products, such as hydrogen peroxide in a basic medium. These oxidizing agents can attack the keratin of the hair, and thus the cosmetic and mechanical properties of the hair can deteriorate considerably in the event of repeated dyeing.

It is also known to dye human keratin fibers by direct dyeing comprising applying to the keratin fibers direct dyes which are colored and dyeing molecules having affinity for the fibers. There may be mentioned, by way of non-limiting examples of direct dyes which are conventionally used, nitro dyes, benzene dyes, anthraquinone dyes, nitropyridine dyes, azo dyes, cationic azo dyes, xanthene dyes, acridine dyes, azine dyes, dyes of the triarylmethane type and natural dyes.

Another method exists for dyeing keratin materials using indandiones, such as 1,2-indandiones and 1,3-indandiones. These dyeing methods are, for example, described in European Patent Application Nos. EP 1010419, EP 1013259, and EP 1300134, and International Patent Application Nos. WO 95/11001 and WO 99/18914.

The colors thus obtained can be very chromatic and may not bring about chemical degradation of keratin, but they have the disadvantage of being only temporary or semi-permanent, that is to say, the colors can fade after only 4 to 5 shampoo washings.

A need therefore exists for systems and methods for dyeing which allow good color-fastness to be obtained without involving the use of oxidizing agents, which are likely to damage keratin materials.

Accordingly, the present disclosure relates to novel dyeing compositions, which make it possible to dye keratin materials, such as the hair, with a color-fastness equivalent or even superior to that obtained by oxidation dyeing. The compositions of the disclosure can be used in the absence of strong oxidizing agents, thereby preserving, for example perfectly, the keratin materials.

The present disclosure therefore relates to a composition for dyeing keratin materials, such as the skin and keratin fibers, comprising, in an appropriate medium, at least one 1,2-indandione derivative chosen from those of formulae (I) and (II)

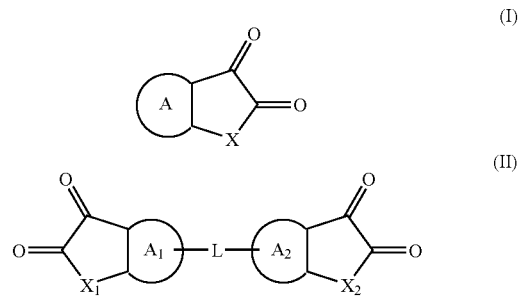

wherein:
- X, X1, and X2, which may be identical or different, are chosen from oxygen atoms, sulphur atoms, phosphorus atoms, and CR1R2 radicals;
- R1 and R2, which may be identical or different, are chosen from hydrogen atoms, halogen atoms, C3-C18 alkyl radicals, alkenyl radicals, carboxyl radicals, hydroxycarbonylalkyl radicals, hydrogenocarbonyl radicals, hydrogenocarbonylalkyl radicals, alkylcarboxyalkyloxy radicals, cyano radicals, thiocyano radicals, nitro radicals, nitroso radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, aryl radicals, heteroaryl radicals, and quaternary ammonium radicals, such as tetraalkylammonium, pyridinium, benzothiazolium or imidazolium;
- A, A1 and A2, which may be identical or different, are chosen from fused and non-fused mono- and polyaromatic radicals comprising from 6 to 50 carbon atoms and which may comprise at least one heteroatom chosen from nitrogen, sulphur, oxygen and/or phosphorus;
- L is chosen from a single bond or an aliphatic or aromatic divalent radical, it being possible for the radical to comprise at least one heteroatom chosen from oxygen, sulphur, nitrogen and phosphorus, and it is possible for the radical to be fused with A1 or A2, with the proviso that the at least one 1,2-indandione derivative chosen from those of formulae (I) and (II) is not chosen from 1,2-indandione:

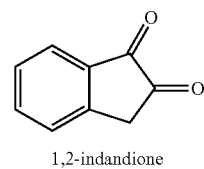

1,2-indandione

The colors thus obtained can exhibit good chromaticity and the compositions can be distinguishable, for instance, due to their weak selectivity and good color-fastness to external agents such as light, shampoos and sweat. Such compositions can be useful for dyeing keratin fibers, such as the hair.

In the above description, the number of carbons ranging from 1 to 18 corresponds, unless otherwise stated, to the number of carbons of the alkyl radicals. When the radical indicated comprises an aryl radical, then the number of carbons can range from 6 to 30 carbons.

As used herein, the term "polyaromatic radical" refers to a radical that comprises at least two aromatic rings, it being possible for the rings of the radical to be fused or non-fused. A monoaromatic radical is a radical which comprises a single aromatic ring.

The rings A, A1 and A2 and also the radicals R1 and R2 may be optionally substituted. When they are substituted, the at least one substituent R can be chosen from, for example, halogens, alkyl groups, alkenyl radicals, carboxyl radicals, alkoxycarbonyls, hydroxycarbonylalkyl radicals, hydrogenocarbonyl radicals, hydrogenocarbonylalkyl radicals, alkylcarboxylalkyloxy radicals, cyano radicals, thiocyano radicals, nitro radicals, nitroso radicals, sulphonato radicals, alkylsulphonamido radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, silyl radicals, alkylsilyl radicals, alkylarylsilyl radicals, arylsilyl radicals, siloxyl radicals, alkylsilyloxy radicals, arylsilyloxy radicals, aryl radicals, heteroaryl radicals, quaternary ammonium radicals, and radicals of the

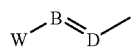

type wherein B and D, which may be identical or different, are chosen from carbon and nitrogen atoms, and wherein W is chosen from a ring of at least 5 members or an aromatic or heteroaromatic, fused or non-fused polycycle, it being possible for the heteroatom to be chosen from nitrogen, oxygen, sulphur and/or phosphorus. In addition, two adjacent radicals on the rings A, A1 or A2 may together form a dioxy bridge —O—CH$_2$—O—.

According to one embodiment of the present disclosure, the groups X, X1 and X2 are chosen from, for example, CR1R2 radicals. For instance, R1 and R2 can be chosen from hydrogen, halogens, such as bromine, alkoxy radicals, alkyl and aryl radicals, or a fused ring.

The rings A, A1 and A2, can be chosen from, for example benzene, naphthalene, anthracene, thiophene, pyridine and quinoline groups. For instance, in one embodiment of the present disclosure, the rings A, A1 and A2 are chosen from benzene, naphthalene, anthracene and pyridine rings.

As disclosed herein, the rings A, A1 and A2 can be optionally substituted with at least one entity chosen from halogen, C1-C6 alkyl, hydroxyl, C1-C6 alkoxy, amino, imidazolyl, pyridinyl, mono- and di(C1-C6 alkyl)amino, mono- and dihydroxy(C1-C6 alkyl)amino and tri(C1-C6 alkyl)ammmonio, thio, (C1-C6 alkyl)thio, thio(C1-C6 alkyl), (C1-C6 alkyl)carbonyl, hydrogenocarbonyl, hydroxycarbonyl, (C1-C6 alkoxy)carbonyl, nitro, and sulphonato radicals and the corresponding protonated groups such as ammonio. imidazolio and/or pyridinio.

In one embodiment of the present disclosure, A, A1 and A2 are chosen so as to form, with the indandione ring, a system of delocalized π electrons.

By way of non-limiting examples of derivatives of formula (I), there may be mentioned

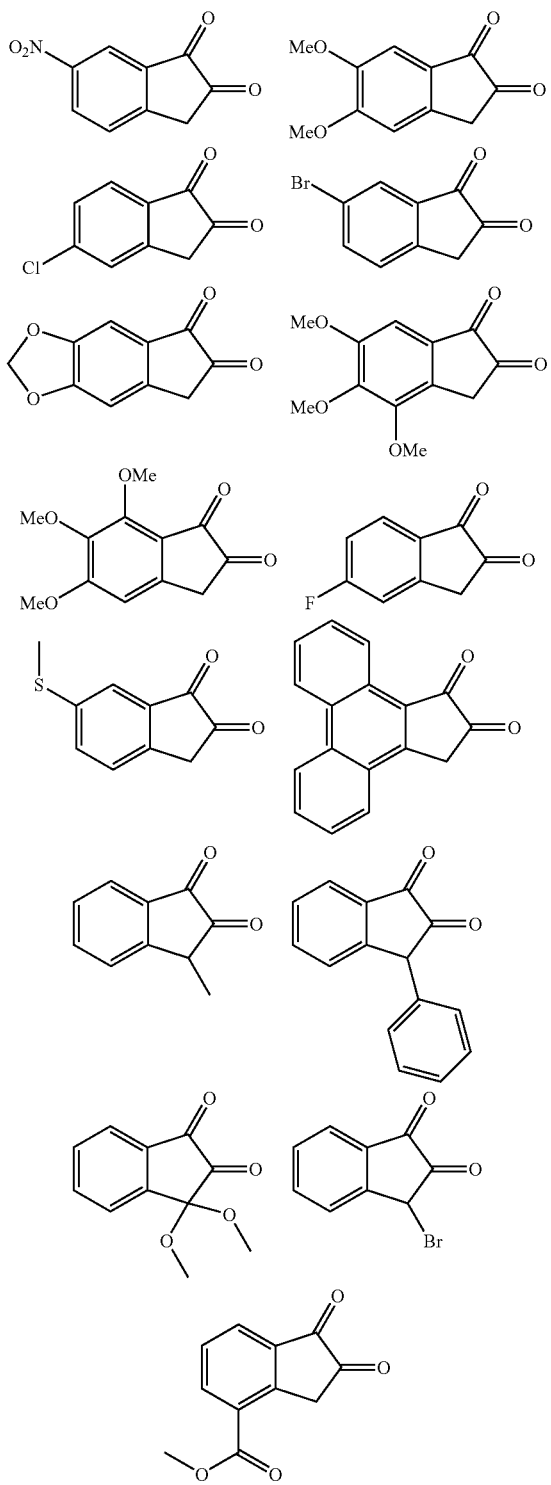

According to another embodiment of the present disclosure, the derivatives of formula (I) have the formula:

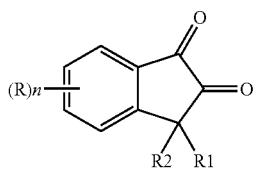

wherein R1 and R2 are as defined above, R is chosen from, for instance, halogens, alkyl radicals, aryl radicals, alkoxy radicals, aryloxy radicals, carboxyl radicals, alkoxycarbonyl radicals, nitro, amino, mono- and dialkylamino radicals, cyano radicals, thiocyano radicals, sulphonato radicals, and alkylsulphonamido radicals, or n, which ranges from 0 to 4, can be equal to 0, 1 or 2. In one embodiment of the present disclosure, R is chosen from halogens, and alkyl and alkoxy radicals.

For the derivatives of formula (II), L can be, for example, chosen from a ring of at least 6 members, or an aromatic or heteroaromatic, fused or non-fused polycycle, it being possible for these rings to be substituted. It is also possible for L to form a ring fused with A1 and/or A2.

The derivatives of formulae (I) and (II) of course also include the corresponding acid addition salts and addition salts with bases.

The 1,2-indandione derivatives chosen from those of formulae (I) and (II) can be obtained from known methods of synthesis, for instance, the syntheses described in International Patent Application No. WO 98/20344, or the article "Design and synthesis of chromogenic and fluorogenic reagents for amino acid detection," O. Petrovskaïa, thesis from the University of Pennsylvania, 1999.

The derivatives of formula (II) may be synthesized based on the teaching of International Patent Application No. WO 98/20344, and for which the connection between the two 1,2-indandione derivatives is realized according to the methods described in the articles "Ninhydrin and ninhydrin analogs, Syntheses and applications," M. M. Joullié, T. R. Thompson, N. H. Nemeroff, Tetrahedron, Vol. 47, No. 42, 8791-8830, (1991); "The total synthesis of Ochrobirine," B. Nalliah, Q. A. Ahmed, R. H. F. Manske, R. Rodrigo, Canadian Journal of Chemistry, 50, 1819 (1972); "Synthesis of Ninhydrin Analogs," R. R. Hark, PhD, Dissertation in chemistry, University of Pennsylvania, 1996.

In accordance with the present disclosure, the 1,2-indandione derivatives of formula (I) described above may be used alone for dyeing keratin materials. Indeed, these compounds are capable of generating colored molecules with the amine functional groups of keratin (colored reaction).

It is also possible to use the compounds of formula (I) together with at least one activator, which makes it possible to modify the kinetics of reaction of the 1,2-indandione derivative with the keratinous material. Such an activator may be an oxidizing agent, a reducing agent, Brönsted acids, a metal catalyst such as catalysts based on a transition metal such as iron, platinum and palladium, proteins, for instance enzymes, compounds which modify the ionic strength of the medium, such as NaCl salts, compounds comprising a labile hydrogen chosen from those comprising a primary or secondary amine functional group and those comprising an activated methylene functional group. It is of course also possible to use a mixture of such compounds.

According to another embodiment of the present disclosure, the chemical activator is a compound comprising a labile hydrogen chosen from the compounds comprising a primary or secondary amino functional group and the compounds comprising an activated methylene functional group. For example, the compounds with a primary amine or a secondary amine functional group can be aromatic amines.

There may be mentioned, by way of non-limiting examples of such aromatic amines, N,N-dimethyl-p-phenylenediamine, N,N-diethyl-p-phenylenediamine, N-(2-hydroxyethyl)-N-ethyl-p-phenylenediamine, N,N-bis(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, dibromohydrate of 2,5-dihydroxy-4-morpholinoaniline, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino) phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino-, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, chosen from those of formula (Ia)

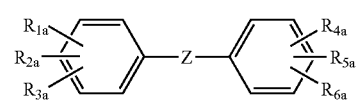

wherein $R_{1a}$ is chosen from hydroxyl and amino groups optionally substituted with a $C_{1-4}$ alkyl, $C_{1-4}$ hydroxyalkyl or $(C_{1-4}$ alkoxy)-$(C_{1-4}$ alkyl) group, $R_{2a}$, $R_{3a}$, $R_{4a}$, $R_{5a}$ and $R_{6a}$, which may be identical or different, are chosen from hydrogen atoms, hydroxyl groups, and amino groups, optionally substituted with a $C_{1-4}$ alkyl, $C_{1-4}$ hydroxyalkyl or $(C_{1-4}$ alkoxy)-$(C_{1-4}$ alkyl) group, or a carboxylic or sulphonic acid group, Z is chosen from a direct bond, $C_{1-4}$ hydrocarbon chains, which can be saturated or unsaturated, optionally hydroxylated, carbonyl, sulphonyl and imino groups, oxygen and sulphur atoms, and groups of formula Q-(CH$_2$—P—CH$_2$-Q')$_y$, wherein P is chosen from a direct bond and groups —CH$_2$- and —CHOH—, Q and Q', which may be identical or different, are chosen from oxygen atoms, NR$_7$ groups wherein R$_7$ is chosen from a hydrogen atom, C$_{1-4}$ alkyl, and C$_{1-4}$ hydroxyalkyl groups, or groups O—(CH$_2$)$_p$NH and NH—(CH$_2$)$_{p'}$—O, wherein p and p' are 2 or 3 and "y" is a number ranging from 1 to 4.

The nonaromatic primary or secondary amines can be chosen from, for example, 2-aminoethanol, 2-methoxyethylamine, 2-ethoxyethylamine, 2-(2-aminoethoxy)ethanol, 2- or 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3diol, tetrahydropentylamine, pentahydroxyhexylamines such as glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine and 3-(2-aminoethylamino) propanol.

The compounds comprising an activated methylene functional group can be chosen, for example, from the following: 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

These primary and secondary amines and these compounds comprising activated methylene functional groups and other compounds comprising a labile hydrogen are also described in German Patent Application Nos. DE 43 17 855, DE 197 17 222, DE 198 45 481, and DE 197 45 355.

When the 1,2-indandione derivatives of formulae (I) and (II) are used in combination with a primary or secondary amine or with a compound comprising an activated methylene functional group, it is necessary to store these different reagents separately in order to avoid a premature color reaction. The reagents are then only brought into contact immediately before application to the hair by freshly mixing two compositions respectively comprising the 1,2-indandione derivatives and the compounds comprising a labile hydrogen or an activated methylene. The reagents may also be brought directly into contact with the hair by applying the various reagents in succession.

The present disclosure also relates to multi-component dyeing agents comprising as a first component, at least one composition (a) comprising at least one 1,2-indandione derivative chosen from those of formulae (I) and (II), and as a second component, at least one composition (b) comprising at least one activator which makes it possible to modify the kinetics of reaction of the 1,2-indandione derivative.

According to one embodiment of the present disclosure, the activator is a compound with a primary or secondary amine functional group, or at least one compound with an activated methylene functional group, as described above.

This multi-component dyeing agent can be provided, for example, in the form of a multi-compartment kit, with at least one first compartment comprising the at least one composition (a) and at least one second compartment comprising the at least one composition (b).

According to the present disclosure, the dyeing composition comprises, in addition to the at least one 1,2-indandione derivative chosen from those of formulae (I) and (II), at least one cosmetic active ingredient.

The at least one cosmetic active ingredient present in the cosmetic compositions of the present disclosure can be chosen from, for example, vitamins; saccharides; oligosaccharides; polysaccharides which are optionally hydrolyzed, or optionally modified; amino acids; oligopeptides; peptides; proteins which are optionally hydrolyzed or optionally modified; polyamino acids; enzymes; fatty acids and alcohols which are optionally branched; animal, vegetable and mineral waxes; ceramides and pseudoceramides; hydroxylated organic acids; UV-screening agents; antioxidants and anti-free-radical agents; chelating agents; antidandruff agents; seborrhoea-regulating agents; soothing agents; cationic, anionic, nonionic and amphoteric surfactants; cationic, anionic, neutral and amphoteric polymers; silicones which are optionally organomodified; mineral, vegetable and animal oils; polyisobutenes and poly($\alpha$-olefins); fatty esters; anionic polymers in dissolved or dispersed form; nonionic polymers in dissolved or dispersed form; reducing agents; solvents; hair dyes such as direct dyes or oxidation dye precursors (bases and/or couplers) different from the claimed compounds comprising a primary or secondary amine functional group; oxidants such as hydrogen peroxide optionally combined with persalts; and pigments.

The at least one cosmetic active ingredient, when present, can be present in an amount ranging from 0.001% to 50% by weight, for instance from 0.01% to 20% by weight, such as in an amount ranging from 0.1% to 10% by weight, relative to the total weight of the cosmetic composition.

In one embodiment of the dyeing cosmetic composition according to the present disclosure, the at least one cosmetic active ingredient is chosen from surfactants and/or polymeric agents (polymer), it being possible for these agents to be of a nonionic, cationic, anionic or amphoteric nature.

The compositions of the present disclosure can have a pH ranging from 2 to 12, such as from 6 to 11.

The at least one 1,2-indandione derivative chosen from those of formulae (I) and (II), can be present in an amount ranging, for example, from 0.0001% to 30% by weight, relative to the total weight of the composition.

The compounds comprising a labile hydrogen or an activated methylene, when they are present in the composition of the invention, can be present, for example, in an amount ranging from 0.0001% to 30% by weight, relative to the total weight of the composition.

The present disclosure additionally relates to a method for dyeing a keratin material, for instance keratin fibers, comprising the application of a composition as described above. The composition is left in contact with the keratin material for a period of leave-in time sufficient to obtain the desired color. This period of leave-in time ranges for example, from 5 minutes to 1 hour, such as from 15 minutes to 30 minutes. The colored reaction between the at least one 1,2-indandione derivative and the amine functional groups of the keratin or the compounds comprising a labile hydrogen or an activated methylene which may optionally be present can be accelerated by heating after application to the keratin material. The heating temperature can be less than or equal to 180° C., such as less than or equal to 60° C.

After obtaining the desired color, the keratin material can be, for example, rinsed and washed.

When compounds comprising a labile hydrogen such as primary or secondary amines, or compounds comprising an activated methylene functional group are used, the application of the reagents taking part in the colored reaction can also be performed in two stages. In other words, it is possible to successively apply at least two different compositions, at least one composition (a) comprising at least one 1,2-indandione derivative chosen from those of formula (I) and at least one composition (b) comprising at least one compound comprising a primary or secondary amine functional group or an activated methylene functional group.

The present disclosure also relates to a two-stage dyeing method comprising applying to the keratin material, at least two compositions one after the other, in any order, at least one composition (a) and at least one composition (b) as defined above for the multi-component dyeing agent.

This separate application of the at least two reactive compositions can have the benefit of avoiding the handling of colored compositions and thus can reduce the risks of staining materials such as clothes.

According to one embodiment of the present disclosure, the dyeing method is a method for dyeing keratin fibers, such as the hair.

It is also possible to insert an intermediate rinsing step between the application of the at least one composition (a) and the application of the at least one composition (b).

In a manner similar to that described above, it is possible to heat the keratin material to which the compositions (a) and/or (b) are applied.

According to another embodiment of the present disclosure, the dyeing methods described above are methods for dyeing keratin fibers, such as the hair.

The present disclosure also relates to the methods for using the compositions described above in dyeing keratin materials, such as the hair.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples are intended to illustrate the present disclosure in a non-limiting manner.

EXAMPLES

The following dyeing compositions were prepared:

| Constituent | Composition 1 | Composition 2 | Composition 3 | Composition 4 |
|---|---|---|---|---|
| Compound 1 | $10^{-2}$ mol | — | — | — |
| Compound 2 | — | $10^{-2}$ mol | — | — |
| Compound 3 | — | — | $10^{-2}$ mol | — |
| Compound 4 | — | — | — | $10^{-2}$ mol |
| Ethanol | 50 g | 50 g | 50 g | 50 g |
| NaOH/HCl | q.s. pH 7 | q.s. pH 7 | q.s. pH 7 | q.s. pH 7 |
| Distilled water | q.s. 100 g | q.s. 100 g | q.s. 100 g | q.s. 100 g |

The structures of the compounds used are given in the table below:

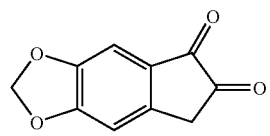

Compound 1

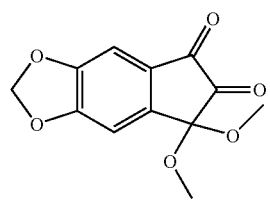

Compound 2

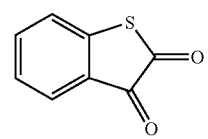

Compound 3

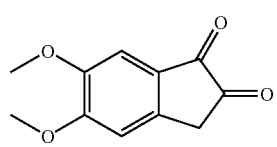

Compound 4

Each composition was applied to a lock of natural grey hair which was 90% white, and to a lock of permanently waved grey hair which was 90% white for a period of 30 minutes, at the temperature of 600° C. After dyeing, the locks were rinsed and dried.

The color of the locks was measured in the L*a*b* system using a spectrocolorimeter (Minolta CM3600d, 10° angle, D65 illuminant, specular components included). According to this system, L* denotes the intensity, a* and b* indicate two color axes: a* indicates the green/red axis and b* the blue/yellow color axis.

The colorimetric results were as given in the table below:

| | | L* | a* | b* | Visual evaluation |
|---|---|---|---|---|---|
| Natural hair | Composition 1 | 51.03 | 15.72 | 39.98 | Coppery |
| | Composition 2 | 51.61 | −1.18 | 7.13 | Grey |

-continued

|  |  | L* | a* | b* | Visual evaluation |
|---|---|---|---|---|---|
|  | Composition 3 | 59.97 | −0.01 | 34.45 | Golden yellow |
|  | Composition 4 | 52.59 | 14.34 | 33.55 | Coppery |
| Permanently waved hair | Composition 1 | 50.52 | 15.84 | 44.24 | Coppery |
|  | Composition 2 | 50.85 | −1.13 | 6.26 | Grey |
|  | Composition 3 | 59.26 | −0.17 | 35.62 | Golden yellow |
|  | Composition 4 | 51.83 | 20.21 | 38.87 | Coppery |

The results demonstrate that these compositions exhibit weak selectivity, i.e., there is very little difference in the dye absorbance between natural and permanently waved hair.

The locks of natural hair thus dyed were subjected to 20 shampoo washings. The color-fastness with respect to repeated washing were measured and the results are given below:

| Natural hair | % degradation* |
|---|---|
| Composition 1 | 4.6 |
| Composition 4 | 16.6 |

The percentage degradation is given by the relationship:

$$\% \text{ degradation} = \frac{?E_{lock\ after\ shampooings/lock\ before\ shampooings}}{?E_{lock\ before\ shampooings/lock\ after\ dyeing}} \times 100$$

What is claimed is:

1. A composition for dyeing keratin materials comprising, in an appropriate medium:
    at least one cosmetic active ingredient, wherein the at least one cosmetic active ingredient is present in an amount ranging from 0.001% to 50% by weight and
    at least one 1,2-indandione derivative chosen from those of formulae (I) and (II):

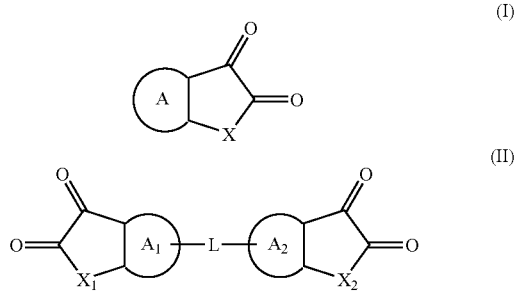

wherein:
    X, X1 and X2, which may be identical or different, are chosen from oxygen atoms, sulphur atoms, phosphorus atoms, and CR1R2 radicals;
    R1 and R2, which may be identical or different, are chosen from hydrogen atoms, halogen atoms, C3-C18 alkyl radicals, alkenyl radicals, carboxyl radicals, hydroxycarbonylalkyl radicals, hydrogenocarbonyl radicals, hydrogenocarbonylalkyl radicals, alkylcarboxyalkyloxy radicals, cyano radicals, thiocyano radicals, nitro radicals, nitroso radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, aryl radicals, heteroaryl radicals, and quaternary ammonium radicals;
    A, A1 and A2, which may be identical or different, are chosen from fused and non-fused mono- and polyaromatic radicals comprising from 6 to 50 carbon atoms and which may comprise at least one heteroatom chosen from nitrogen, sulphur, oxygen and/or phosphorus;
    L is chosen from a single bond or aliphatic and aromatic divalent radicals, it being possible for the radical to comprise at least one heteroatom chosen from oxygen, sulphur, nitrogen and phosphorus and to be fused with A1 or A2,
    with the proviso that the at least one 1,2-indandione derivative chosen from those of formulae (I) and (II) is not chosen from 1,2-indandione

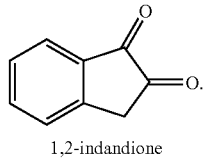

1,2-indandione

2. The composition according to claim 1, wherein the rings A, A1 and A2, and the radicals R1 and R2 are substituted with R, wherein R is chosen from halogens, alkyl groups, alkenyl radicals, carboxyl radicals, alkoxycarbonyl radicals, hydroxycarbonylalkyl radicals, hydrogenocarbonyl radicals, hyd rogenocarbonylalkyl radicals, alkylcarboxyalkyloxy radicals, cyano radicals, thiocyano radicals, nitro radicals, nitroso radicals, suiphonato radicals, alkylsulphonamido radicals, hydroxyl radicals, hydroxyalkyl radicals, alkoxy radicals, C1-C18 alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, silyl radicals, C1-C18 alkylsilyl radicals, alkylarylsilyl radicals, arylsilyl radicals, siloxyl radicals, alkylsilyloxy radicals, arylsilyloxy radicals, aryl radicals, heteroaryl radicals, quaternary ammonium radicals, and radicals of the

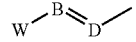

type wherein B and D, which may be identical or different, are chosen from carbon and nitrogen atoms and wherein W is chosen from a ring of at least 5 members, or an aromatic or heteroaromatic, fused or non-fused polycycle, it being possible for the heteroatom to be chosen from nitrogen, oxygen, sulphur and/or phosphorus;
    and wherein, optionally, two adjacent radicals on the rings A, A1 or A2 can together form a dioxy bridge
    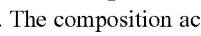.

3. The composition according to claim 1, wherein X, X1 and X2, which may be identical or different, are chosen from $CR_1R_2$ radicals.

4. The composition according to claim 3, wherein R1 and R2, which may be identical or different, are chosen from hydrogen atoms, halogen atoms, alkoxy radicals, alkyl radicals, aryl radicals, and fused rings.

5. The composition according to claim 1, wherein the rings A, A1 and A2, which may be identical or different, are chosen from benzene, naphthalene, anthracene, thiophene, pyridine and quinoline groups.

6. The composition according to claim 5, wherein the rings A, A1 and A2, which may be identical or different, are chosen from benzene, naphthalene, anthracene and pyridine rings.

7. The composition according to claim 2, wherein the rings A, A1 and A2, which may be identical or different, are optionally substituted with at least one entity chosen from halogen atoms, and $C_1$-$C_6$ alkyl, hydroxyl, $C_1$-$C_6$ alkoxy, amino, imidazolyl, pyridinyl, mono- and di($C_1$-$C_6$ alkyl) amino, mono- and dihydroxy(C1-C6 alkyl)amino, and tri (C1-C6alkyl)ammmonio, thio, ($C_1$-$C_6$ alkyl)thio, thio($C_1$-$C_6$ alkyl), ($C_1$-C6 hydrogenocarbonyl, hydroxycarbonyl, ($C_1$-$C_6$ alkoxy)carbonyl, nitro, and suiphonato radicals and the corresponding protonated groups.

8. The composition according to claim 1, wherein A, A1 and A2, which may be identical or different, are chosen so as to form, with the indandione ring, a system of delocalized π electrons.

9. The composition according to claim 1, wherein the at least one 1,2-indandione derivative is chosen from those of the formulae:

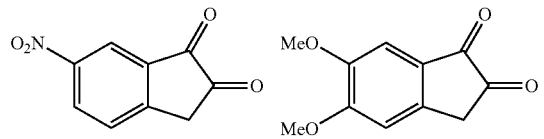
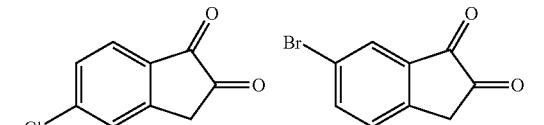
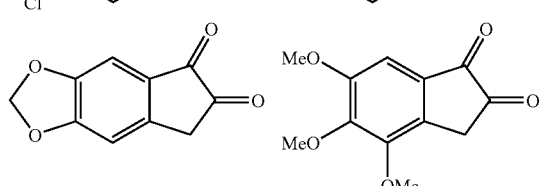
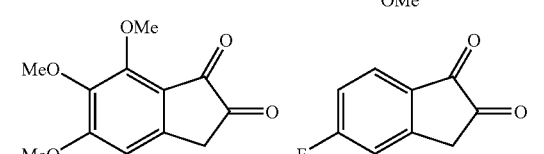
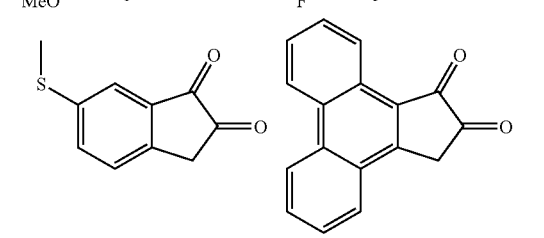

10. The composition according to claim 1, wherein the at least one 1,2-indandione derivative is chosen from the derivatives of formula (I) with the formula:

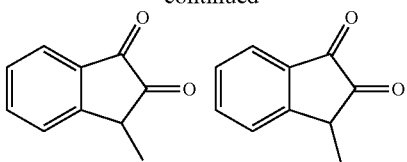
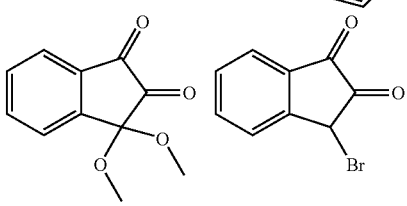
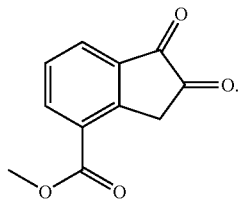
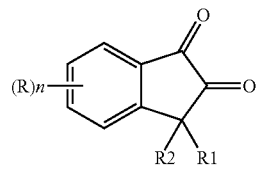

wherein
R1, R2, which may be identical or different, are chosen from hydrogen atoms, halogen atoms, C3-C18 alkyl radicals, alkenyl radicals, carboxyl radicals, hydroxycarbonylalkyl radicals, hydrogenocarbonyl radicals, hydrogenocarbonylalkyl radicals, alkylcarboxyalkyloxy radicals, cyano radicals, thiocyano radicals, nitro radicals, nitroso radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, aryl radicals, heteroaryl radicals, and quaternary ammonium radicals;

R is chosen from halogens, alkyl groups, alkenyl radicals, carboxyl radicals, alkoxycarbonyl radicals, hydroxycarbonylalkyl radicals, hydrogenocarbonyl radicals, hydrogenocarbonylalkyl radicals, alkylcarboxyalkyloxy radicals, cyano radicals, thiocyano radicals, nitro radicals, nitroso radicals, sulphonato radicals, alkylsulphonamido radicals, hyd roxyl radicals, hydroxyalkyl radicals, alkoxy radicals, C1-C18 alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, silyl radicals, C1-C18 alkylsilyl radicals, alkylarylsilyl radicals, arylsilyl radicals, siloxyl radicals, alkylsilyloxy radicals, arylsilyloxy radicals, aryl radicals, heteroaryl radicals, quaternary ammonium radicals, and radicals of the

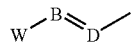

type wherein B and D, which may be identical or different, are chosen from carbon and nitrogen atoms and wherein W is chosen from a ring of at least 5 members, or an aromatic or heteroaromatic, fused or non-fused polycycle, it being possible for the heteroatom to be chosen from nitrogen, oxygen, sulphur and/or phosphorus; and n ranges from 0 to 4.

11. The composition according to claim 10, wherein R is chosen from halogens, alkyl radicals, aryl radicals, alkoxy radicals, aryloxy radicals, carboxyl radicals, alkoxycarbonyl radicals, nitro, amino, mono- and dialkylamino radicals, cyano radicals, thiacyano radicals, sulphonato radicals, and alkylsulphonamido radicals, or n is equal to 0.

12. The composition according to claim 11, wherein R is chosen from halogens, and alkyl and alkoxy radicals.

13. The composition according to claim 1, wherein, in the derivatives of formula (II), L is chosen from rings of at least 6 members, or an aromatic or heteroaromatic, fused or non-fused polycycle, it being possible for these rings to be substituted.

14. The composition according to claim 13, wherein the derivatives of formula (II) are such that L forms a ring fused with A1 and/or A2.

15. The composition according to claim 1, further comprising at least one compound comprising a functional group chosen from primary and secondary amino functional groups and activated methylene functional groups.

16. The composition according to claim 15, wherein the at least one compound comprising a primary or secondary amine functional group is an aromatic amine chosen from N,N-dimethyl-p-phenylenediamine, N,N-diethyl-p-phenylenediamine, N-(2-hydroxyethyl)-N-ethyl-p-phenylenediamine, N,N-bis(2-hydroxyethyl)-p-phenylenediamine, N-(2-methoxyethyl)-p-phenylenediamine, 2,3-, 2,4-or 2,5-dichloro-p-phenylenediamine, 2-chloro-p-phenylenediamine, dibromohydrate of 2,5-dihydroxy-4-morpholinoaniline, 2-, 3- or 4-aminophenol, 2-aminomethyl-4-aminophenol, 2-hydroxymethyl-4-aminophenol, orthophenylenediamine, p-phenylenediamine, orthotoluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- or 4-aminophenylacetic acid, 2,3-, 2,4-, 2,5-, 3,4- or 3,5 diaminobenzoic acid, 4-amino- or 5-aminosalicylic acid, 3-amino-4-hydroxybenzoic acid, 4-amino-3-hydroxybenzoic acid, 2-amino-, 3-amino-, or 4-aminobenzenesulphonic acid, 3-amino-4-hydroxybenzenesulphonic acid, 4-amino-3-hydroxynaphthalene-1-suiphonic acid, 6-amino-7-hydroxynaphthalene-2-sulphonic acid, 7-amino-4-hydroxynaphthalene-2-suiphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diam ino-4-hydroxypyrocatechol, aromatic anilines, and aromatic phenols comprising another aromatic residue chosen from those of formula (Ia):

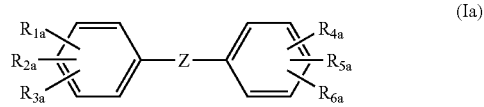

wherein $R_{1a}$ is chosen from hydroxyl and amino groups optionally substituted with a $C_{1-4}$ alkyl, $C_{1-4}$ hydroxyalkyl or ($C_{1-4}$ alkoxy)-($C_{1-4}$ alkyl) group, $R_{2a}$, $R_3$, $R_{4a}$, $R_{5a}$ and $R_{6a}$, which may be identical or different, are chosen from hydrogen atoms, hydroxyl groups and amino groups, optionally substituted with at least one entity chosen from $C_{1-4}$ alkyl, $C_{1-4}$ hydroxyalkyl and ($C_{1-4}$ alkoxy)-($C_{1-4}$ alkyl) groups, or a carboxylic or suiphonic acid group, Z is chosen from a direct bond, and $C_{1-4}$ hydrocarbon chains which are saturated or unsaturated, optionally hydroxylated, and carbonyl, suiphonyl and imino groups, oxygen and sulphur atoms, and groups of formula Q-($CH_2$-P—$CH_2$Q')y where P is chosen from a direct bond or —$CH_2$- and —CHOH— groups, Q and Q', which may be identical or different, are chosen from oxygen atoms, and $NR_7$ groups where $R_7$ is chosen from a hydrogen atom, $C_{1-4}$alkyl and $C_{1-4}$ hydroxyalkyl groups, and O—$(CH_2)_p$NH and NH—$(CH_2)_p$—O groups wherein p and p' are equal to 2 or 3, and "y" is a number ranging from 1 to 4.

17. The composition according to claim 16, wherein the nonaromatic primary or secondary amines are chosen from 2-aminoethanol, 2-methoxyethylam me, 2-ethoxyethylamine, 2-(2-aminoethoxy)ethanol, 2- or 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hyd roxymethylpropane-1,3-diol, tetrahydropentylamine, pentahyd roxyhexylam ines, 1,2-diaminoethane, 1,2- or 1,3-diaminopropane, 1,3-diamino-2-propanol, 2-(2-aminoethylamino) ethylamine, 2-(2-aminoethylamino)ethanol, 3-(2-aminoethylamino)propylamine and 3-(2-aminoethylamino) propanol.

18. The composition according to claim 17, wherein the pentahydroxyhexylamines are chosen from such as glucamine, D-glucosamine, and D-galactosamine.

19. The composition according to claim 15, wherein the compound with an activated methylene functional group is chosen from 1,2,3,3-tetramethyl-3H-indolium iodide, 1,2,3, 3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-acetic acid, 1-ethyl-2-quinaldinium iodide, 1-methyl-2-quinaldinium iodide, barbituric acid, thiobarbituric acid, 1,3-dimethylthiobarbituric acid, diethyithiobarbituric acid, oxindole, 3-indoxyl acetate, coumarin, and 1-methyl-3-phenyl-2-pyrazi none.

20. The composition according to claim 1, wherein the composition has a pH ranging from 2 and 12.

21. The composition according to claim 20, wherein the composition has a pH ranging from 6 to 11.

22. The composition according to claim 1, wherein the at least one 1,2-indandione derivative chosen from those of formulae (I) and (II) is present in an amount ranging from 0.0001% to 30% by weight, relative to the total weight of the composition.

23. The composition according to claim 15, wherein the at least one compound comprising at least one functional group chosen from activated methylene functional groups, or primary and secondary amine functional groups, is present in an amount ranging from 0.0001% to 30% by weight, relative to the total weight of the composition.

24. The composition according to claim 1, further comprising at least one surfactant and/or one polymeric agent of a nonionic, cationic, anionic or amphoteric nature.

25. A multi-component dyeing agent comprising
as a first component, at least one composition (a) comprising at least one 1,2-indandione derivative chosen from those of formulae (I) and (II):

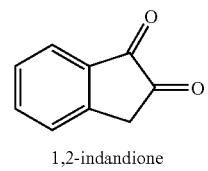

(I)

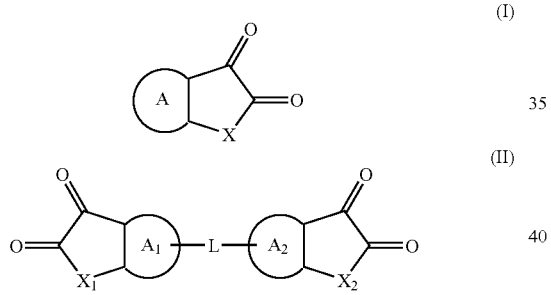

(II)

wherein:
X, X1 and X2, which may be identical or different, are chosen from oxygen atoms, sulphur atoms, phosphorus atoms, and CR1 R2 radicals;
R1 and R2, which may be identical or different, are chosen from hydrogen atoms, halogen atoms, C3-C18 alkyl radicals, alkenyl radicals, carboxyl radicals, hydroxycarbonylalkyl radicals, hydrogenocarbonyl radicals, hyd rogenocarbonylalkyl radicals, alkylcarboxyalkyloxy radicals, cyano radicals, thiocyano radicals, nitro radicals, nitroso radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, aryl radicals, heteroaryl radicals, and quaternary ammonium radicals;
A, A1 and A2, which may be identical or different, are chosen from fused and non-fused mono- and polyaromatic radicals comprising from 6 to 50 carbon atoms and which may comprise at least one heteroatom chosen from nitrogen, sulphur, oxygen and/or phosphorus;

L is chosen from a single bond or aliphatic and aromatic divalent radicals, it being possible for the radical to comprise at least one heteroatom chosen from oxygen, sulphur, nitrogen and phosphorus and to be fused with A1 or A2, with the proviso that the at least one 1,2-indandione derivative chosen from those of formulae (I) and (II) is not chosen from 1,2-indandione

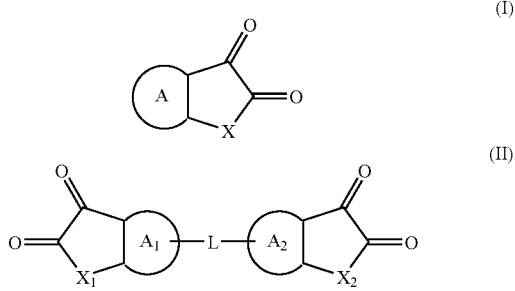

1,2-indandione and
as a second component, at least one composition (b) comprising at least one activator for modifying the kinetics of reaction of the 1,2-indandione derivative.

26. The multi-component dyeing agent according to claim 25, wherein the at least one activator is at least one compound comprising at least one functional group chosen from primary and secondary amine functional groups or at least one compound with an activated methylene functional.

27. A method for dyeing keratin material, comprising:
applying to the keratin material a dyeing composition, comprising, in an appropriate medium, at least one 1,2-indandione derivative chosen from those of formulae (I) and (II):

(I)

(II)

wherein:
X, X1 and X2, which may be identical or different, are chosen from oxygen atoms, sulphur atoms, phosphorus atoms, and CR1R2 radicals;
R1 and R2, which may be identical or different, are chosen from hydrogen atoms, halogen atoms, C3-C18 alkyl radicals, alkenyl radicals, carboxyl radicals, hydroxycarbonylalkyl radicals, hydrogenocarbonyl radicals,
hyd rogenocarbonylalkyl radicals, alkylcarboxyalkyloxy radicals, cyano radicals, thiocyano radicals, nitro radicals, nitroso radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylamino radicals, thio radicals, alkylthio radicals, arylthio radicals, alkenylthio radicals, aryl radicals, heteroaryl radicals, and quaternary ammonium radicals;

A, A1 and A2, which may be identical or different, are
chosen from fused and non-fused mono- and polyaromatic radicals comprising from 6 to 50 carbon atoms
and which may comprise at least one heteroatom chosen from nitrogen, sulphur, oxygen and/or phosphorus;

L is chosen from a single bond or aliphatic and aromatic
divalent radicals, it being possible for the radical to
comprise at least one heteroatom chosen from oxygen,
sulphur, nitrogen and phosphorus and to be fused with
A1 or A2, with the proviso that the at least one 1,2-indandione derivative chosen from those of formulae (I) and (II) is not chosen
from 1,2-indandione

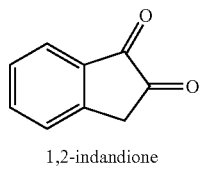

1,2-indandione and leaving the composition on the keratin material for a
period of time sufficient to allow the desired color to be
obtained.

28. The method for dyeing keratin material according to
claim 27, further comprising heating the keratin material to
which the dyeing composition is applied, to at least a
temperature of 80° C.

29. The dyeing method according to claim 28, further
comprising heating the keratin material to which the dyeing
composition is applied, to a temperature of at least 60° C.

30. A method for dyeing keratin material comprising,
applying to the keratin material, at least two compositions
one after the other, in any order, the at least two compositions being at least one composition (a) comprising at least one
1,2-indandione derivative chosen from those of formulae (I) and (II):

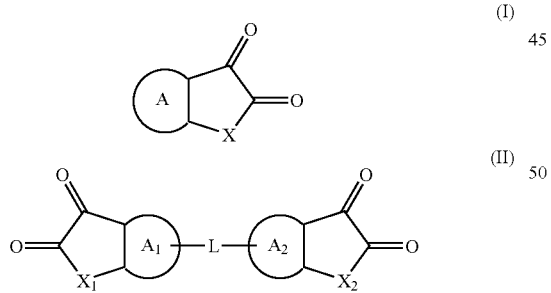

wherein:
X, X1 and X2, which may be identical or different, are
chosen from oxygen atoms, sulphur atoms, phosphorus
atoms, and CR1 R2 radicals;
R1 and R2, which may be identical or different, are
chosen from hydrogen atoms, halogen atoms, C3-C18
alkyl radicals, alkenyl radicals, carboxyl radicals, hyd
roxycarbonylalkyl radicals, hyd rogenocarbonyl radicals,
hydrogenocarbonylalkyl radicals, alkylcarboxyalkyloxy
radicals, cyano radicals, thiocyano radicals, nitro radicals, nitroso radicals, hydroxyl radicals, hydroxyalkyl
radicals, alkoxy radicals, alkenyloxy radicals, aryloxy
radicals, amino radicals, alkylamino radicals, dialkylamino radicals, arylalkylamino radicals, diarylamino
radicals, alkenylamino radicals, thio radicals, alkylthio
radicals, arylth io radicals, alkenylthio radicals, aryl
radicals, heteroaryl radicals, and quaternary ammonium radicals;

A, A1 and A2, which may be identical or different, are
chosen from fused and non-fused mono- and polyaromatic radicals comprising from 6 to 50 carbon atoms
and which may comprise at least one heteroatom chosen from nitrogen, sulphur, oxygen and/or phosphorus;
L is chosen from a single bond or aliphatic and aromatic
divalent radicals, it being possible for the radical to
comprise at least one heteroatom chosen from oxygen,
sulphur, nitrogen and phosphorus and to be fused with
A1 or A2,
with the proviso that the at least one 1,2-indandione derivative chosen from those of formulae (I) and (II) is not chosen
from 1,2-indandione

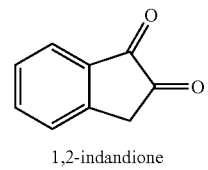

1,2-indandione and
at least one composition (b) comprising at least one
activator for modifying the kinetics of reaction of the
1,2-indandione derivative.

31. The method for dyeing according to claim 30, wherein
the keratin material is rinsed step between the application of
the at least two compositions: at least one composition (a)
and the at least one composition (b), applied in any order.

32. The method for dyeing according to claim 27, wherein
the keratin material is keratin fibers.

33. The method for dyeing according to claim 30, wherein
the keratin material is keratin fibers.

34. A multi-compartment kit for dyeing keratin material,
comprising,
at least one first compartment comprising at least one
composition (a) comprising at least one 1,2-indandione
derivative chosen from those of formulae (I) and (II):

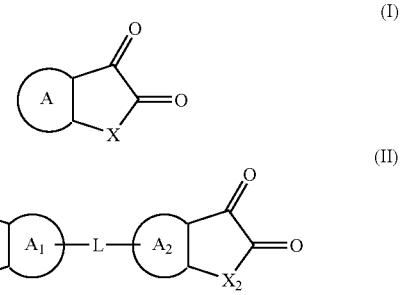

wherein:
X, X1 and X2, which may be identical or different, are
chosen from oxygen atoms, sulphur atoms, phosphorus
atoms, and CR1 R2 radicals;

R1 and R2, which may be identical or different, are chosen from hydrogen atoms, halogen atoms, C3-C18 alkyl radicals, alkenyl radicals, carboxyl radicals, hydroxycarbonylalkyl radicals, hydrogenocarbonyl radicals, hydrogenocarbonylalkyl radicals, alkylcarboxyalkyloxy radicals, cyano radicals, thiocyano radicals, nitro radicals, nitroso radicals, hydroxyl radicals, hydroxyalkyl radicals, alkoxy radicals, alkenyloxy radicals, aryloxy radicals, amino radicals, alkylamino radicals, dialkylamino radicals, arylalkylamino radicals, diarylamino radicals, alkenylam mo radicals, thio radicals, alkylthio radicals, arylth io radicals, alkenylthio radicals, aryl radicals, heteroaryl radicals, and quaternary ammonium radicals;

A, A1 and A2, which may be identical or different, are chosen from fused and non-fused mono- and polyaromatic radicals comprising from 6 to 50 carbon atoms and which may comprise at least one heteroatom chosen from nitrogen, sulphur, oxygen and/or phosphorus;

L is chosen from a single bond or aliphatic and aromatic divalent radicals, it being possible for the radical to comprise at least one heteroatom chosen from oxygen, sulphur, nitrogen and phosphorus and to be fused with A1 or A2, with the proviso that the at least one 1,2-indandione derivative chosen from those of formulae (I) and (II) is not chosen from 1,2-indandione

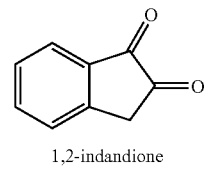

1,2-indandione and at least one second compartment comprising at least one composition (b) comprising at least one activator for modifying the kinetics of reaction of the 1,2-indandione derivative.

* * * * *